United States Patent
Bergmann et al.

(10) Patent No.: US 6,432,393 B1
(45) Date of Patent: *Aug. 13, 2002

(54) HAIR CARE COMPOSITIONS WHICH PROVIDE HAIR BODY AND WHICH COMPRISE ELASTOMERIC RESINOUS MATERIALS

(75) Inventors: Wolfgang Robert Bergmann, Long Grove; John Edward Wydila, Schaumburg; Ben Janchitraponvej, Niles; Paul Howard Neill, Hinsdale; Chaitanya Umedbhai Patel, Glen Ellyn, all of IL (US); Christophe Michel Finel, Compiegne (FR); Walter Thomas Gibson, Cheshire; Roger Michael Lane, Heswall, both of (GB)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,487

(22) Filed: Jun. 5, 1998

(51) Int. Cl.⁷ .............................. A61K 7/06; A61K 6/00; A61K 7/00; A61K 7/11
(52) U.S. Cl. .................. 424/70.1; 424/401; 424/70.12; 514/63
(58) Field of Search .............................. 424/401, 70.1, 424/70.12; 514/63

(56) References Cited

U.S. PATENT DOCUMENTS

| 4,842,850 A | 6/1989 | Vu |
| 4,902,499 A | 2/1990 | Bolish, Jr. et al. |
| 5,385,729 A | * 1/1995 | Prencipe et al. |
| 5,635,469 A | * 6/1997 | Fowler et al. |
| 5,654,362 A | 8/1997 | Schulz, Jr. et al. |
| 5,721,026 A | 2/1998 | Feder et al. |

FOREIGN PATENT DOCUMENTS

| EP | 0001462 | 4/1979 |
| EP | 0412705 | 2/1991 |
| EP | 0473039 | 3/1992 |
| EP | 0584877 | 3/1994 |

OTHER PUBLICATIONS

International Search Report Application No. PCT/EP 99/03588 mailed Oct. 19, 1999.

* cited by examiner

Primary Examiner—Thurman K. Page
Assistant Examiner—Humera N. Sheikh
(74) Attorney, Agent, or Firm—Matthew Boxer

(57) ABSTRACT

The invention relates to aqueous hair care compositions including conditioners, shampoos, and mousses. The invention also relates to methods of treating hair, and more particularly to treating hair with aqueous hair care compositions which contain one or more elastomeric resinous materials. These materials when tested at the same concentration that could be incorporated into a product exhibit a G' modulus between $1 \times 10^2$ and $1 \times 10^5$ dynes/cm². Furthermore these resins when mixed with a hydrophilic or hydrophobic diluent at a ratio of 1:95 to 95:1% and this mixture then incorporated into an aqueous emulsion in the range of 0.1 to 10% have been demonstrated to deliver a consumer perceptible increase in hair body without sacrificing conditioning attributes.

20 Claims, No Drawings

HAIR CARE COMPOSITIONS WHICH PROVIDE HAIR BODY AND WHICH COMPRISE ELASTOMERIC RESINOUS MATERIALS

BACKGROUND OF THE INVENTION

The present invention is directed to hair care compositions which supply body to the treated hair without giving up conditioning attributes. More particularly, the present invention is directed to hair care compositions and a method for treating hair which supply body to the treated hair without giving up conditioning attributes. In the past, it has been difficult to achieve good hair body from a hair treatment composition without giving up conditioning attributes. Moreover, while styling would ordinarily be considered a measure of hair body, prior art compositions have failed to deliver good styling attributes. The present invention overcomes these deficiencies. Other products in the market give either body or conditioning. The present invention gives both body and conditioning.

U.S. Pat. No. 4,902,299 to Bolich et al. teaches styling benefits, which may not provide the combination of body and conditioning, from rigid silicone polymers having complex viscosities greater than $10^7$ poise when delivered from a rinse-off product (shampoo or conditioner). They also require a volatile carrier which is typically a linear or cyclic silicone or hydrocarbon. This volatile carrier exhibits a solubility in water of less than 0.1% and is present at a level between 0.1 and 99.9% However, we have measured the complex modulus of the SR-545 material described in the patent and determined that at $5.28 \times 10^{-2}$ dynes/cm$^2$ it is four orders of magnitude lower than the materials in our invention.

U.S. Pat. No. 4,842,850 to Vu teaches styling benefits from a rigid silicone polymer contained in a shampoo. He also claims a volatile silicone carrier at a range from 1–10% of the total composition.

PCT/EP96/01462 Birtwistle et al., which is hereby incorporated by reference, teaches a hair care composition containing a non-rigid emulsion polymerized cross linked conditioning agent having a viscosity between $10^6$–$10^9$ cts.

SUMMARY OF THE INVENTION

The present invention is directed to hair care compositions which supply body to the treated hair without giving up conditioning attributes. More particularly, the present invention is directed to hair care compositions and a method for treating hair which supply body to the treated hair without giving up conditioning attributes. In the past, it has been difficult to achieve good hair body from a hair treatment composition without giving up conditioning attributes. Moreover, while styling would ordinarily be considered a measure of hair body, prior art compositions have failed to deliver good styling attributes. The present invention overcomes these deficiencies.

More specifically, this invention relates to aqueous or non-aqueous hair care compositions including conditioners, shampoos, and mousses. Conditioners include rinse-off and leave-in conditioners. The invention also relates to methods of treating hair, and more particularly to treating hair with aqueous hair care compositions which contain one or more elastomeric resinous materials. These materials when tested at the same concentration that would be incorporated into a product exhibit a G' modulus between $1 \times 10^2$ and $1 \times 10^5$ dynes cm$^2$. Furthermore these resins when mixed with a hydrophilic or hydrophobic diluent at a ratio of 1:95 to 95:1% and this mixture then incorporated into an aqueous emulsion in the range of 0.1 to 10% have been demonstrated to deliver a consumer perceptible increase in hair body without sacrificing conditioning attributes.

DETAILED DESCRIPTION OF THE INVENTION

The present invention relates to aqueous and non-aqueous hair care compositions including for example, conditioners, shampoos, hair sprays and mousses. Conditioners include rinse-off and leave-in conditioners. The invention also relates to methods of treating hair, and more particularly to treating hair with aqueous hair care compositions which contain one or more elastomeric resinous materials. As noted above, these elastomeric materials when tested at the same concentration that would be incorporated into a product exhibit a G' modulus between $1 \times 10^2$ and $1 \times 10^5$ dynes/cm$^2$. Furthermore these resins when mixed with a hydrophilic or hydrophobic diluent at a ratio of 1:95 to 95:1% and this mixture then incorporated into an aqueous emulsion in the range of 0.1 to 10% have been demonstrated to deliver a consumer perceptible increase in hair body without sacrificing conditioning attributes.

Previous work has demonstrated that silicone resins of high viscosity $10^5$–$10^9$ poise are required to yield styling benefits from a rinse off product (Bolich et al., Birtwistle et al. and Vu). All of our previous work indicates that styling is an important component of body in the consumers' mind. Thus, one would expect that a material that is capable of delivering styling would also deliver body. However, we have found that not all resins in the $10^5$–$10^9$ poise range are capable of delivering on consumer perceptible body. Additionally, resins that fall well below the $10^5$–$10^9$ poise range also deliver on body. What we have found, unexpectedly, is that it is not the viscosity of the neat resin that determines if it will deliver body. What is important is the viscosity of the resin when mixed with a hydrophilic or hydrophobic diluent that is then incorporated into the final formulation.

The one or more elastomeric resinous materials that can be included in our compositions are any elastomers that have the G' and G" measurements set forth in this specification. These elastomers include non-silicone elastomers or more preferably cross-linked or uncross-linked silicone elastomers.

Moreover, the degree of crosslinking of silicone elastomers affects their performance in the compositions of the invention. Preferred silicone elastomers for ;use in the invention are polydiorganosiloxanes, preferably derived from suitable combinations of $R_3SiO_{0.5}$ units and $R_2SiO$ units where each R independently represents an alkyl, alkenyl (e.g. vinyl), alkaryl, aralkyl, or aryl (e.g. phenyl) group. R is most preferably methyl.

The preferred crosslinked silicone elastomers of the invention are cross-linked polydimethyl siloxanes (which have the CTFA designation dimethicone), optionally having end groups such as hydroxyl or methyl.

One preferred elastomer of the invention is DC 2-9040.

DC 2-9040 Cross-linking Chemistry is as follows.

The cross linker used in the DC 2-9040 is an alpha, omega aliphatic diene of the following structure: $CH_2=CH(CH_2)_xCH=CH_2$, where X ranges from 1–20. A gel is formed by crosslinking and addition of Si—H across double bonds in the alpha, omega-diene. The following Dow Corning patent describes the DC 2-9040: U.S. Pat. No. 5,654,362. This just mentioned U.S. patent is hereby incorporated by reference.

Another preferred elastomer of the invention is DC 3-2365.

The structure of the cross-linker used in DC 3-2365 is given below:

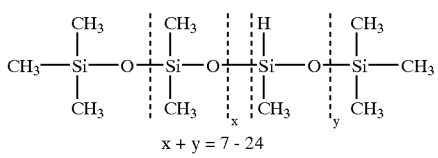

x + y = 7 - 24

Another preferred elastomer of the invention is Silicone/Urethane Copolymer.

The structure of the urethane cross-linker is given below:

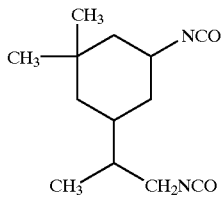

The tradename for the silicone-urethane copolymer is Polyderm PPI-SI-100. The supplier is Alzo Incorporated, Matawan, N.J.

The degree of crosslinking of the silicone elastomers is suitably from about 0.05% to about 35%, preferably being in the range of about 0.15% to about 7%, e.g. from about 0.2 to about 2%.

Suitable emulsion polymerized cross-linked silicone elastomers are commercially available or can be readily made using conventional techniques well known to those skilled in the art.

G' and G" are well-recognized moduli that are used in measuring the physical properties of viscoelastic fluids as can be seen from "Viscoelastic Fluids" Ronald Darby pages 106 through 115, published by Marcel Dekker, Inc. (1976) which are hereby incorporated by reference.

G' and G" are components of the complex modulus, G*, that is used to characterize the viscoelastic behavior of polymers. G' represents the elastic or solid-like character of the polymer, and G" represents the viscous or liquid-like character of the polymer. The G' and G" components of the complex modulus are derived from relationships between the oscillatory stress and the oscillatory strain.

The G' and G" rheological measurements were carried out using a Bohlin VOR rheometer (Bohlin Instruments, Inc.). Two measuring geometries were used. The choice of geometries is based on the viscosity and the volume of the material to be measured. For lower viscosity polymer fluids, such as GE SR 1000 in 50% DC 245 and Dow Corning X2-1787, the C25 cup and bob geometry was employed. The diameter of the bob was 25 mm with a gap spacing of 1.25 mm. For higher viscosity polymer fluids, such as DC 2-9040 in DC 245 and Polyderm PPI-SI-100 in Myristyl Ether Propionate, the parallel plate geometry was used. The diameter of the upper plate was 30 mm and the gap spacing of 1 mm was used. All tests were run at 25° C.

In carrying out a dynamic viscosity measurement, the first step was to establish the viscoelastic region. Initially, the strain amplitude at constant frequency was increased and the moduli were plotted versus the amplitude in order to establish the linear viscoelastic region. Once the viscoelastic region was established, oscillatory measurements were carried out at one amplitude within the linear viscoelastic region as a function of frequency. The Bohlin VOR rheometer is capable of covering the frequency range of 0.01 to 125 rad/sec.

From the stress, $t_o$, and strain, $g_o$, amplitudes, and from the phase-angle, delta, the following expressions are derived:

$$|G^*| = \frac{\tau_o}{\gamma_o}$$

$G' = |G^*|\cos \delta$ $G'' = |G^*|\sin \delta$ $|G^*| = G' + iG''$ where G* is the complex modulus, G' the storage modulus (elastic component of G*), G" is the loss modulus (viscous component of G') and i is equal to $(-1)^{1/2}$.

The elastomeric resinous materials used in the compositions have G' and G" measured after they are mixed with the hydrophilic or hydrophobic diluent and before the final product is prepared.

The G' modulus of these elastomeric resinous materials after the mixing with diluent is about $1 \times 10^2$ to $1 \times 10^7$ dynes/cm$^2$ or, more preferably, $1 \times 10^2$ to $1 \times 10^5$ dynes/cm$^2$. The G" modulus of these elastomeric resinous materials after mixing with diluent is about $1 \times 10^2$ to $1 \times 10^5$ dynes/cm$^2$ or, more preferably, $1 \times 10^2$ to $1 \times 10^4$ dynes/cm$^2$.

As noted above, in compositions of our invention the elastomeric resinous materials are mixed with a hydrophilic or hydrophobic diluent such as PPG-2 Myristyl Ether Propionate or cyclomethicone.

The weight ratio of elastomeric resinous material to diluent may run from about 1:95 to about 95:1.

The mixture is then made into an aqueous emulsion wherein the resulting elastomer concentration is in a weight per cent range of about 0.1 to about 10%. In making our compositions, conventional means known to those skilled in the art are employed.

Our hair care compositions include rinse-off conditioners, leave-on conditioners, shampoos and mousses, sprays, or lotions. Particularly preferred forms are conditioners having conditioning and bodifying properties.

Hair conditioner compositions of the invention may comprise one or more cationic surfactants.

Examples of cationic surfactants include mono or di or tri alkyl quaternary ammonium compounds. Additional surfactants include quaternary ammonium hydroxides or cetyl pyridinium hydroxides or salts thereof. Specific cationic surfactants include quaternary ammonium hydroxides, such as tetramethylammonium hydroxide, alyltrimethylammonium hydroxides wherein the alkyl group has from about 8 to 22 carbon atoms, for example octyltrimethylammonium hydroxide, dodecyltrimethylammonium hydroxide, hexadecyl trimethylammonium hydroxide, cetyltrimethylammonium hydroxide, octyldimethylbenzylammonium hydroxide, decyldimethylbenzylammonium hydroxide, stearyldimethylbenzylammonium hydroxide, didodecyidimeth ylammonium hydroxide, dioctadecyldimethylammonium hydroxide, tallow trimethylammonium hydroxide, cocotrimethylammonium hydroxide, cetyltrimethylammonium chloride, dicetyldimethylammonium chloride, tricetylmethylammonium chloride and the corresponding salts thereof, for example, chlorides.

Other cationic surfactants include amidoamines, cetylpyridinium hydoxide or salts thereof, for example chlorides; or compounds selected from the group consisting of Quaternium-5, Quaternium-31, Quaternium-18, and mixtures thereof.

In hair conditioning compositions of the invention, the level of cationic surfactant is preferably 0.01 to 10%, or 0.05 to 5%, or 0.1 to 2% by weight of the composition.

Another ingredient that may be advantageously incorporated into hair treatment compositions of the invention which are conditioners is a fatty alcohol, particularly in conditioning compositions of the invention which comprise one or more cationic surfactant materials. Preferred fatty alcohols comprise from 8 to 22 carbon atoms, more particularly from 16 to 20. Examples of fatty alcohols include cetyl alcohol and stearyl alcohol. Compositions of the invention which are conditioners can include a conditioning agent such as a fatty amine like stearamidopropyl dimethylamine.

Hair treatment compositions of the invention may also contain one or more conditioning agents selected from the group consisting of cationic polymers, protein hydrolyzates and quaternised protein hydrolyzates.

Another preferred hair treatment composition in accordance with the invention is a shampoo composition which, in addition to the silicone elastomer further comprises a surfactant to provide a deterging benefit. The deterging surfactant is selected from anionic, nonionic, amphoteric and zwitterionic surfactants, and mixtures thereof.

Suitable anionic surfactants include the alkyl sulphates, alkyl ether sulfates, alkaryl sulfonates, alkanoyl isethionates, alkyl succinates, alkyl sulphosuccinates, n-alkoyl sarcosinates, alkyl phosphates, alkyl ether sulphonates, alkyl ether carboxylates and alpha-olefin sulphonates, especially their sodium, magnesium, ammonium, and mono-, di-, and tri-ethanolamine salts. The alkyl and acyl groups generally contain from 8 to 18 carbon atoms and may be unsaturated. The alkyl ether sulphates, alkyl ether phosphates and alkyl ether carboxylates may contain from one to ten ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl sulphate, sodium lauryl isethionate and sodium lauryl sarcosinate. The most preferred anionic surfactants are sodium lauryl sulphate, triethanolamine lauryl sulphate, triethanolamine monolauryl phosphate, sodium lauryl ether sulphate 1EO, 2EO, and 3EO, ammonium lauryl sulphate and ammonium lauryl ether sulphate 1EO, 2EO, 3EO.

Nonionic surfactants suitable for use in compositions of the invention may include condensation products of aliphatic (8 to 18 carbons) primary, secondary linear or branched chain alcohols or phenois with alkylene oxides, usually ethylene oxide and generally having from 6 to 30 ethylene oxide groups. Other suitable nonionics include alkanolamides. Examples include coco mono- diethanolamide and coco mono-isopropanolamide.

Amphoteric and zwitterionic surfactants suitable for use in compositions of the invention may include alkyl amine oxides, alkyl betaines, alkyl amidopropyl betaines, alkylsulphobetaines, alkyl glycinates, alkyl carboxyglcinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine, lauryl betaine, cocamidopropyl betaine and sodium cocamphopropionate.

The surfactants are present in shampoo compositions of the invention in an amount from 0.1% to 50% by weight, preferably 0.5% to 30% by weight.

A further optional component of compositions of the invention which are shampoos, is a deposition aid, generally present at 0.001% to 5%. Examples of such deposition aids include polyquaternium-16; cationic guars, and polymer JR resins.

Compositions of the invention which are shampoos may further comprise from 0.1 to 5% of a suspending agent such as Carbopol 910, Carbopol 940, Carbopol 941, acrylate copolymers, or poly saccharides.

Small quantities of surfactant ranging anywhere from 0.1 to about 10%, preferably from 0.1 to about 1%, may be present in the hair mousse compositions of the invention the surfactant may be anionic, nonionic or cationic emulsifier. Surfactants which are suitable for mousses include, for example, sodium cocoyl isethionate and Laureth 20.

Depending on the type of composition employed, one or more additional ingredients conventionally incorporated into hair treatment compositions may be included in compositions of the invention. Such additional ingredients include styling agents such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturizing agents, herb or other plant extracts and other natural ingredients.

Compositions of the invention can include a pH buffer like citric acid.

Compositions of the invention can include a dispersing agent such as water-insoluble alkyl esters and derivatives such as PPG2 Myristyl ether propionate, or cyclomethicone or polyhydric compounds such as glycerin.

Compositions of the invention can optionally include an opacifier.

Our invention includes a method for giving hair unexpected body as well as conditioning which comprises treating said hair with compositions of our invention.

The following examples serve to illustrate and not to limit the scope of the present invention.

Examples Formulations
Rinse-off Condition (1)

| Component | Concentration, % Active |
| --- | --- |
| Stearyl Alcohol and Ceteareth-20 | 1.00 |
| Cetyl Alcohol | 3.25 |
| Stearamidopropyl Dimethylamine | 0.50 |
| Citric Acid (50%) | 0.092 |
| Polyurethane/Silicone 100% (Active) (PPI-SI-100) | 1.50 |

-continued

Examples Formulations
Rinse-off Condition (1)

| Component | Concentration, % Active |
|---|---|
| PPG2 Myristyl Ether Propionate | 1.00 |
| Water | qs. to 100% |
| Viscosity 4500 cps., pH 5.2, Product stable for more than 24 hours | |

All the examples were prepared using softened water.

Manufacturing Instructions
Rinse-off Conditioner (1)

| Step # | Operation |
|---|---|
| 1 | Prepare Pre-Mix ( Polyurethane/Silicone) with PPG2 Myristyl Ether Propionate prior to compounding the batch. Pre-mix is prepared with high agitation and mixed until lump free. |
| 2 | Into a separate vessel, add water and heat to 70–75 C. |
| 3 | With moderate mixing add Steryl Alcohol and Ceteareth-20, Cetyl Alcohol, Stearamidopropyl Dimethylamine, and Citric Acid |
| 4 | Cool batch to 55–50 C. |
| 5 | Add Pre-mix to batch. |
| 6 | Continue cooling to room temperature. |

Rinse-off Conditioner (2)

| Component | Concentration, % Active |
|---|---|
| Stearyl Alcohol and Ceteareth-20 | 1.00 |
| Cetyl Alcohol | 3.25 |
| Stearamidopropyl Dimethylamine | 0.50 |
| Citric Acid (50%) | 0.092 |
| DC 2-9040 | 9.38 |
| Water | qs. to 100% |
| Viscosity 15,000 cps., RV, pH 5.7, Product stable for more than 24 hours Batch homogenized until tree of particles | |

Rinse-off Conditioner (2)

| Step # | Operation |
|---|---|
| 1 | Add water and heat to 70–75 C. |
| 2 | With moderate mixing add Stearyl Alcohol and Ceteareth-20, Cetyl Alcohol, Stearamidopropyl Dimethylamine, and Citric Acid and mix until homogeneous and free of particles. |
| 4 | Cool batch to ambiant temperature. |
| 5 | Add DC 2-9040 |
| 6 | Homogenize to uniform consistency. |

Rinse-off Conditioner (3)

| Component | Concentration, % Active |
|---|---|
| Stearyl Alcohol and Ceteareth-20 | 1.00 |
| Cetyl Alcohol | 3.25 |
| Stearamidopropyl Dimethylamine | 0.50 |
| Citric Acid (50%) | 0.092 |
| Polyisobutylene (50%) emulsion | 0.25 |
| Water | qs. to 100% |
| Viscosity 5,500 cps. RV, pH 5.4, Product stable for more than 24 hours | |

Rinse-off Conditioner (3)

| Step # | Operation |
|---|---|
| 1 | Add water and heat to 70–75 C. |
| 2 | Add Steryl Alcohol and Ceteareth-20, Cetyl Alcohol, Stearamidopropyl Dimethylamine, and Citric Acid and mix until homogeneous and free of particles. |
| 4 | Cool batch to 50 C. |

-continued

Manufacturing Instructions

| 5 | Add Polyisobutylene emulsion. |
|---|---|
| 6 | Continue cooling to room temperature. |

Rinse-off Conditioner (4)

| Component | Concentration, % Active |
|---|---|
| Stearyl Alcohol and Ceteareth-20 | 1.00 |
| Cetyl Alcohol | 3.25 |
| Stearamidopropyl Dimethylamine | 0.50 |
| Citric Acid (50%) | 0.092 |
| DC 2-1391 Silicone (30%) emulsion | 1.50 |
| Water | qs. to 100% |
| Viscosity 5,500 cps. RV, pH 6.0, Product stable for more than 24 hours | |

Rinse-off Conditioner (4)

| Step # | Operation |
|---|---|
| 1 | Add water and heat to 70–75 C. |
| 2 | Add Stearyl Alcohol and Ceteareth-20, Cetyl Alcohol, Stearamidopropyl Dimethylamine, and Citric Acid and mix until homogeneous and free of particles. |
| 4 | Cool batch to 50 C. |
| 5 | Add Dow Corning 2-1391 Silicone. |
| 6 | Continue cooling to room temperature. |

Leave-in Conditioner (1)

| Component | Concentration, % Active |
|---|---|
| Stearyl Alcohol and Ceteareth-20 | 1.00 |
| Cetyl Alcohol | 1.50 |
| Stearamidopropyl Dimethylamine | 0.50 |
| Citric Acid (50%) | 0.092 |
| Polyurethane/Silicone 100%(PPI-SI-100) | 0.50 |
| PPG2 Myristyl Ether Propionate | 0.50 |
| Water | qs. to 100% |
| Viscosity 1,200 cps. RV, pH 5.0, Product stable for more than 24 hours | |

Leave-in Conditioner (2)

| Component | Concentration, % Active |
|---|---|
| Stearyl Alcohol and Ceteareth-20 | 1.00 |
| Cetyl Alcohol | 1.50 |
| Stearamidopropyl Dimethylamine | 0.50 |
| Citric Acid (50%) | 0.092 |
| DC 2-1391(30% emulsion) | 1.50 |
| Water | qs. to 100% |
| Viscosity 1,350 cps. RV, pH 5.7, Product stable for more than 24 hours | |

Leave-in Conditioner (3)

| Component | Concentration, % Active |
|---|---|
| Stearyl Alcohol and Ceteareth-20 | 1.00 |
| Cetyl Alcohol | 1.50 |
| Stearamidopropyl Dimethylamine | 0.50 |
| Citric Acid | 0.092 |
| Polyisobutylene (50% emulsion) | 0.25 |
| Water | qs. to 100% |
| Viscosity 1,375 cps. RV, pH 5.9, Product stable for more than 24 hours | |

Leave-in Conditioner (4)

| Component | Concentration, % Active |
|---|---|
| Stearyl Alcohol and Ceteareth-20 | 1.00 |
| Cetyl Alcohol | 1.50 |
| Stearamidopropyl Dimethylamine | 0.50 |
| Citric Acid | 0.092 |
| DC 2-9040 | 4.69 |
| Water | qs. to 100% |
| Viscosity 5,000 cps. RV, pH 5.8, Product stable for more than 24 hours | |

Manufacturing Instructions

Leave-in Conditioners

| Example | Operations |
|---|---|
| Leave-in Conditioner (1) | Same as Rinse-off Conditioner (1) |
| Leave-in Conditioner (2) | Same as Rinse-off Conditioner (4) |
| Leave-in Conditioner (3) | Same as Rinse-off Conditioner (3) |
| Leave-in Conditioner (4) | Same as Rinse-off Conditioner (2) |

Shampoo (1)

| Component | Concentration, % Active |
|---|---|
| Sodium Laureth Sulfate (2 mole E.O) | 12.50 |
| Cocoamide DEA | 4.00 |
| Polyurethane/Silicone (PPI-SI-100) | 1.50 |
| Citric Acid (50%) | 0.15 |
| PPG-2 Myristyl Ether Propionate | 1.00 |
| Water | qs. to 100% |

Viscosity 2,000 cps. RV, pH 6.1, Product stable for more than 8 hours

Shampoo (1)

| Step # | Operation |
|---|---|
| 1 | Prepare Pre-mix (Polyurethane/Silicone) with PPG2 Myristyl Ether Propionate prior to compounding the batch. Pre-mix is prepared with high agitation and mixed until lump free. |
| 2 | Into a separate vessel add water. |
| 3 | With moderate mixing add Sodium Laureth Sulfate (2 mole E.O.), Cocoamide DEA, and Citric acid. |
| 4 | Add Pre-mix. |
| 5 | Add Pre-mix to batch. |
| 6 | Continue cooling to room temperature. |

Shampoo (2)

| Component | Concentration, % Active |
|---|---|
| Sodium Laureth Sulfate (2 mole E.O) | 12.50 |
| Cocoamide DEA | 4.00 |
| Polyisobutylene | 0.20 |
| Citric Acid (50%) | 0.15 |
| Water | qs. to 100% |

Viscosity 1,150 cps. RV, pH 5.9, Product stable for more than 8 hours

Shampoo (2)

| Step # | Operation |
|---|---|
| 1 | Add water. |
| 2 | With moderate mixing add Sodium Laureth Sulfate (2 mole E.O.), Cocoamide DEA, Polyisobutylene, and Citric acid. |

Shampoo (3)

| Component | Concentration, % Active |
|---|---|
| Sodium Laureth Sulfate (2 mole E.O) | 12.5 |
| Cocoamide DEA | 4.00 |
| DC 2-1391(30% emulsion) | 1.50 |
| Citric Acid | 0.075 |
| Water | qs. to 100% |

Viscosity 875 cps. RV: pH 6.0. Product stable for more than 8 hours

Shampoo (3)

| Step # | Operation |
|---|---|
| 1 | Add water |
| 2 | With moderate mixing add Sodium Laureth Sulfate (2 mole E.O.), Cocoamide DEA, Dow Corning 2-1391, and Citric acid. |

Manufacturing Instructions

Mousse

| Component | Concentration, % Active |
|---|---|
| Stearamidopropyl Dimethylamine | 0.50 |
| Stearyl Alcohol and Ceteareth-20 | 1.00 |
| Polyurethane/Silicone 100%(PPI-SI-100) | 1.50 |
| PPG-2 Myristyl Ether Propionate | 1.00 |
| Cetyl Alcohol | 3.25 |
| Silicone Fluid 245 | 1.80 |
| Propellant HC 50 | 10.0 |
| Citric Acid | 0.092 |
| Water | qs to 100% |

Mousse

| Step # | Operation |
|---|---|
| 1 | Prepare Pre-mix (Polyurethane/Silicone) with PPG2 Myristyl Ether Propionate prior to compounding the batch. Pre-mix is prepared with high agitation and mixed until lump free. |
| 2 | Into a separate vessel add water and heat to 70–75 C. |
| 3 | With moderate mixing add Stearamidopropyl Dimethylamine, Stearyl Alcohol and Ceteareth-20, and Cetyl Alcohol. |
| 4 | Cool to 50 C and add Pre-mix, Silicone Fluid 245. and Citric Acid |
| 5 | Cool batch to room temperature. |
| 6 | Charge propellant. |

Salon Blitz Testing

The following Salon Blitz Testing table is a summary of the results from a series of salon tests conducted over a period of approximately 12 weeks. The benchmark for this studies is the best selling commercial extra body conditioner in the North American market. These data indicate that the formulations containing DC 2-9040 (Ex A.), Silicone/Urethane (Ex. B.) and Polyisobutylene (Ex. F) outperformed the Benchmark formulation in both overall conditioning and in their ability to deliver hair body as reported by the models. The X2-1787 resin (Ex. C.), DC2-1391 (MOD)-High MW resin (Ex. D.) and Silicone Gum Blend 33/67 (Ex. G) did not show any body attribute benefit over the Benchmark. Both the formulations containing DC-9040 (Ex. A) and the Silicone/Urethane (Ex. B) have G' modulus values in the discovered range while the DC-1787 prototype exhibited a very low modulus.

The test results were obtained by using the following method: Salon Blitz Protocol Salon Blitz utilizes female conditioner users as the panelists. In a salon, a professional hair stylist will apply the test product to ½ of the head and the benchmark product to the other side of the panelist's head. Once product is applied, the stylist distributes the product evenly and rinses it out taking care to keeping both sides separated. The panelists then are asked to dry and style their own hair. A questionnaire is provided to each panelist asking them to rate (on a 9 point scale) hair characteristics (e.g. conditioning and body) for both the left and right side of the head. Typically at least 12 panelists (n ranges from 15–100) are recruited for each test product evaluation. Higher values for key characteristics such as conditioning or body indicates a higher intensity for these attributes.

| Compositions | Benchmark % Actives | Ex. A % Active | Ex B % Active | Ex C % Active | Ex D % Active | Ex. E % Active | Ex. F % Active | Ex. G % Active |
|---|---|---|---|---|---|---|---|---|
| Stearamidopropyl Dimethylamine | 0.50 | 0.50 | 0.50 | 0.50 | 0.50 | 0.50 | 0.50 | 0.50 |
| Liquid Citric Acid | 0.092 | 0.092 | 0.092 | 0.092 | 0.092 | 0.092 | 0.092 | 0.092 |
| Propylene Glycol | 0.50 | 0.50 | 0.50 | 0.50 | 0.50 | 0.50 | 0.50 | 0.50 |
| Dicetyldimonium Chloride | 1.43 | 1.43 | 1.40 | 1.43 | 1.43 | 1.43 | 1.43 | 1.43 |
| Stearyl Alcohol and Ceteareth-20 | 1.00 | 1.00 | 1.00 | 1.00 | 1.00 | 1.00 | 1.00 | 1.00 |
| Cetyl Alcohol | 3.25 | 3.25 | 3.25 | 3.25 | 3.25 | 3.25 | 3.25 | 3.25 |
| Silicone Fluid 245 | 1.80 | 7.88 | 1.80 | 1.80 | 1.80 | 7.88 | 1.80 | 1.80 |
| Dimethicone | 0.10 | 0.10 | 0.10 | 0.10 | 0.10 | 0.10 | 0.10 | 0.10 |
| PPG-2 Myristyl Ether Propionate | none | none | 1.00 | none | none | none | none | none |
| Silicone/Urethane (PPI-SI-100) | none | none | 1.50 | none | none | none | none | none |
| DC 2-9040 (16% actives) | none | 1.50 | none | none | none | none | none | none |
| DC-1787 (50%) | none | none | none | 1.5 | none | none | none | none |
| DC2-1391 (MOD)-HIGH MW. | none | none | none | none | 1.5 | none | none | none |
| Silicone Gum Blend 33/67 | none | none | none | none | none | none | none | 1.5 |
| Polyisobutylene | none | none | none | none | none | none | 0.2 | none |
| Chelating Agent, Potassium Chloride, Fragrance, Preservatives and Water | qs to 100 | qs to 100 | qs to 100 | qs to 100 | qs to 100 | qs to 100 | qs to 100 | qs to 100 |
| Conditioning Attribute | 6.6, n = 95 | 6.7, n = 45 | 7.0, n = 32 | 6.1, n = 16 | 6.4, n = 15 | 6.7, n = 15 | 7.1, n = 12 | 6.3, n = 17 |
| Body Attribute | 5.9, n = 95 | 6.2, n = 45 | 6.7, n = 32 | 5.3, n = 16 | 6.0, n = 15 | 6.1, n = 15 | 6.6, n = 12 | 6.0, n = 17 |

Consumer Sensory Testing

The data presented in the table below summarizes the conditioning and body attribute results from a larger scale take home study. Again the formulation containing DC-9040 was demonstrated to provide superior conditioning and body benefit versus the commercial body conditioner. These data confirm the results from the smaller salon test described above.

The below test results were obtained by using the following method:

Consumer Sensory Test (CST) Protocol

The CST format utilizes female conditioner users to participate in a home use study. The benchmark or prototype samples are randomly distributed to the panelists. The samples are blinded to avoided any branding bias. Each participant will take the sample home and use as they would their normal conditioner for 1 week period. After the one week usage period the panelist fills out a questionnaire asking them to rate (on a 9 point scale) the characteristics of the sample just used. Another sample is provided to the participant and used for 1 week. At the completion of the second week the panelist will fill out an identical questionnaire asking them to rate (same scale) the characteristics of the second sample just used. Typically at least 50 panelists (n ranges from 50–75) are recruited for each test product evaluation. Higher values for key characteristics such as conditioning or body indicates a higher intensity for these attributes.

| Compositions | Benchmark % Actives | Ex. A % Active | Ex. F % Active |
|---|---|---|---|
| Stearamidopropyl Dimethylamine | 0.50 | 0.50 | 0.50 |
| Liquid Citric Acid | 0.092 | 0.092 | 0.092 |
| Propylene Glycol | 0.50 | 0.50 | 0.50 |
| Dicetyldimonium Chloride | 1.43 | 1.43 | 1.43 |
| Stearyl Alcohol and Cetereth-20 | 1.00 | 1.00 | 1.00 |
| Cetyl Alcohol | 3.25 | 3.25 | 3.25 |
| Silicone Fluid 245 | 1.80 | 7.88 | 1.80 |
| Dimethicone | 0.10 | 0.10 | 0.10 |
| PPG-2 Myristyl Ether Propionate | none | none | none |
| Silicone/Urethane (PPI-SI-100) | none | none | none |
| DC 2-9040 (16% actives) | none | 1.5 | none |
| DC1787 (50%) | none | none | none |
| DC2-1391 (MOD)-HIGH MW. | none | none | none |
| Silicone Gum Blend 33/67 | none | none | none |
| Polyisobutylene | none | none | 0.2 |
| Chelate Agent, Potassium Chloride, Fragrance, Preservatives and Water | qs to 100 | qs to 100 | qs to 100 |
| Conditioning Attribute | 5.3, n = 57 | 6.0, n = 52 | 5.5, n = 56 |
| Body Attributes | 5.1, n = 57 | 5.5, n = 52 | 5.3, n = 56 |

Complex Moduli for Selected Resins in our Study

The table below lists the G' and G" moduli that have been completed thus far for the formula tested in our salon test and referred to in the literature. Those samples falling in the G' range of $1 \times 10^2$ to $1 \times 10^5$ (DC-9040 and Silicone/Polyurethane) have been shown in both in-house and take home consumer test to deliver both conditioning and body relative to a commercial bodyfing conditioner. The X2-1787 material which falls in a range well below that of our invention has been demonstrated not to deliver consumer recognizable conditioning or body. The GE SR-1000 moduli are included to demonstrate the difference between our invention and that of Bolich et al. The G' modulus of their material $5.2\times10^{-2}$ clearly differentiates our invention from theirs.

| Complex Moduli of Silicone Polymer Dispersions | | |
|---|---|---|
| Complex Moduli @ 0.1 rad/sec | G' dynes/cm$^2$ | G" dynes/cm$^2$ |
| 10% DC 2-9040 in DC 245 | 9.49E+03 | 1.35E+03 |
| 16% DC 2-9040 in DC 245 | 4.38E+04 | 1.69E+03 |
| 60% Si-Polyurethane in Myristyl Ether Propionate | 2.10E+03 | 4.62E+02 |
| GE SR 1000* in 50% DC 245 | 5.28E-02 | 7.72E-01 |
| Dow Corning X2-1787, 50% Aqueous Emulsion | 7.84E+00 | 4.70E+00 |

*SR 1000 is the SR 545 polymer that has been stripped of toluene.

What is claimed is:

1. A non-aqueous hair care composition which comprises one or more elastomeric resinous materials having a G' modulus after mixing with diluent of about $1\times10^2$ to about $1\times10^7$ dynes/cm$^2$ and a G" modulus after mixing with diluent of about $1\times10^2$ to about $1\times10^5$ dynes/cm$^2$.

2. A hair care composition according to claim 1, wherein the G' modulus after mixing with diluent is about $1\times10^2$ to about $1\times10^5$ dynes/cm$^2$.

3. A hair care composition according to claim 1, wherein the G" modulus after mixing with diluent is about $1\times10^2$ to about $1\times10^4$ dynes/cm$^2$.

4. A hair care composition according to claim 1, wherein the elastomeric resinous material is a silicone polymer.

5. A hair care composition according to claim 4, wherein the elastomeric resinous material is a silicone polymer having as a crosslinker an alpha, omega aliphatic diene of the following structure: $CH_2=CH(CH_2)_xCH=CH_2$, where X ranges from 1–20.

6. A hair care composition according to claim 4, wherein the silicone polymer is a compound of the formula:

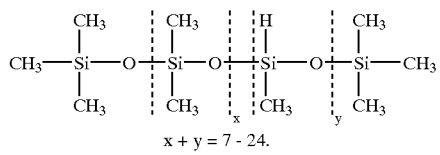

$x + y = 7 - 24$.

7. A hair care composition according to claim 1, in the form of a rinse-off conditioner, leave-on conditioner, a shampoo, a mousse, a spray, or a lotion.

8. A hair care composition according to claim 1, further comprising a surfactant selected from the group consisting of cationic, anionic, nonionic, amphoteric and zwitterionic surfactants, and mixtures thereof.

9. A hair care composition according to claim 8, wherein the anionic surfactant is selected from the group consisting of alkyl sulphates, alkyl ether sulfates, alkaryl sulfonates, alkanoyl isethionates, alkyl succinates, alkyl sulphosuccinates, n-alkoyl sarcosinates, alkyl phosphates, alkyl ether sulphonates, alkyl ether carboxylates and alpha-olefin sulphonates, and their sodium, magnesium, ammonium, and mono-, di-, and tri-ethanolamine salts.

10. A hair care composition according to claim 8, wherein the cationic surfactant is alkyl pyridinium, amine, or alkyl quaternary compounds or mixtures thereof.

11. A hair care composition according to claim 10, wherein the cationic surfactant is an alkyl quaternary ammonium compound.

12. A hair care composition according to claim 1, wherein the weight ratio of the elastomeric resinous material to the diluent is from about 1:95 to 95:1.

13. A hair care composition according to claim 1, wherein the concentration of the elastomeric resinous material is 0.1 to 10 weight %.

14. A method for giving hair body which comprises treating said hair with a hair care composition according to claim 1.

15. A method according to claim 14, in the form of a rinse-off conditioner, leave-on conditioner, a shampoo, a mousse, a spray, or a lotion.

16. A method according to claim 14, wherein the hair care composition further comprises a surfactant selected from the group consisting of cationic, anionic, nonionic, amphoteric and zwitterionic surfactants, and mixtures thereof.

17. A method according to claim 14, wherein the anionic surfactant is selected from the group consisting of alkyl sulphates, alkyl ether sulfates, alkaryl sulfonates, alkanoyl isethionates, alkyl succinates, alkyl sulphosuccinates, n-alkoyl sarcosinates, alkyl phosphates, alkyl ether sulphonates, alkyl ether carboxylates and alpha-olefin sulphonates, and their sodium, magnesium, ammonium, and mono-, di-, and tri-ethanolamine salts.

18. A method according to claim 14, wherein the cationic surfactant is an alkyl quaternary ammonium compound.

19. A hair care composition according to claim 1, where said one or more elastomeric resinous materials have a G' modulus after mixing with hydrophilic or hydrophobic diluent of about $1\times10^2$ to about $1\times10^7$ dynes/cm$^2$ and a G" modulus after mixing with hydrophilic or hydrophobic diluent of about $1\times10^2$ to about $1\times10^5$ dynes/cm$^2$.

20. A hair care composition according to claim 1 which further comprises PPG-2 Myristyl ether propionate.

* * * * *